United States Patent [19]

Turner

[11] Patent Number: 5,088,487
[45] Date of Patent: Feb. 18, 1992

[54] BODY WRAP WITH POCKET FOR PLIABLE FROZEN COMPOSITION

[75] Inventor: Ronald L. Turner, Golden, Colo.

[73] Assignees: Cecil R. Jackson, Mesa; Gerald L. Collard, Case Grande; Catheryn L. Macon, Phoenix, all of Ariz.

[21] Appl. No.: 578,195

[22] Filed: Sep. 6, 1990

[51] Int. Cl.⁵ ............................................. A61F 7/00
[52] U.S. Cl. ................................. 128/402; 128/403; 62/530
[58] Field of Search ............... 128/379, 380, 399, 402, 128/403; 62/530; 383/901

[56] References Cited

U.S. PATENT DOCUMENTS

| | | | |
|---|---|---|---|
| 3,736,769 | 6/1973 | Petersen | 62/530 |
| 4,527,566 | 7/1985 | Abare | 128/402 |
| 4,596,250 | 6/1986 | Beisang, III et al. | 128/402 |
| 4,865,012 | 9/1989 | Kelley | 128/403 |

FOREIGN PATENT DOCUMENTS 0046894 3/1982 European Pat. Off. ............ 128/403

*Primary Examiner*—Edward M. Coven
*Assistant Examiner*—Mark S. Graham
*Attorney, Agent, or Firm*—Tod R. Nissle

[57] ABSTRACT

A flexible wrap for maintaining a thermal pack in heat transfer relation to the human anatomy. The thermal pack contains a quantity of liquid and filler particles which, when the liquid is frozen solid, produces a pliable thermal pack which conforms to contoured surfaces of the human body.

13 Claims, 1 Drawing Sheet

BODY WRAP WITH POCKET FOR PLIABLE FROZEN COMPOSITION

This invention relates to heat transfer apparatus.

More particularly, the invention relates to a flexible wrap for maintaining a thermal pack in heat transfer relation to the human anatomy, the thermal pack containing a quantity of liquid which, when frozen solid, is pliable and will conform to a contoured surface of the human body.

In a further respect, the invention relates to a flexible wrap which maintains a frozen material in heat transfer relation with the human body, the material having a heat of fusion which is greater than that of water.

Various types of bands which are wrapped around a portion of the human body to cool the body are well known in the art. See, for example, U.S. Pat. No. 4,614,189 to MacKenzie, U.S. Pat. No. 4,326,533 to Henderson, U.S. Pat. No. 3,159,160 to Ullom, and U.S. Pat. No. 4,527,566 to Abare. Such prior art devices ordinarily maintain a cold fluid or fluid-solid slush in heat transfer relationship with a selected portion of the body. In U.S. Pat. No. 4,527,566 to Abare, crushed ice is utilized. Ullom, in his U.S. Pat. No. 3,159,160, appears to use cold water. In U.S. Pat. No. 4,326,533 to Henderson, frozen water can be utilized in a series of relatively small, linked articulating containers. Henderson also refers to the use of a gel or a solution of propylene glycol and water or of a brine solution which turns into a semi-liquid slush when cooled. Henderson's gel or semi-liquid slushes are used when "more flexibility" is desired in the band which is wrapped about a portion of the body. Henderson is, therefore, recognizing a problem inherent in most, if not all, prior art body wraps. Once the fluid in the wrap is completely frozen solid, the resulting solid is rigid and will not conform to the body. Maintaining a solid piece of ice or some other frozen substance against the body can be uncomfortable and can also, since the entire surface area of the piece of ice normally is not immediately adjacent to the body, be a relatively inefficient way of cooling the body. The prior art solutions to this problem are noted above and include using crushed ice, using a slush, using a band comprised of a series of small articulated containers, and simply using cold water. The ease of manufacture and efficiency of a cooling wrap for the human body would be significantly improved if the fluid utilized in the wrap could be frozen solid and would, when frozen solid, still be pliable enough to readily conform to a portion of the human body.

Accordingly, it would be highly desirable to provide an improved cooling wrap for the human body, the wrap maintaining in heat transfer relation with the human body a liquid which, after being frozen solid, is sufficiently pliable to be manually contoured to a selected portion of the human body.

Therefore, it is a principal object of the invention to provide improved heat transfer apparatus.

A further object of the invention is to provide an improved cooling wrap for the human body, the wrap including a liquid which in its frozen state is sufficiently pliable to be manually contoured to the human body.

These and other, further and more specific objects and advantages of the invention will be apparent to those skilled in the art from the following detailed description thereof, taken in conjunction with the drawings, in which.

Briefly, in accordance with my invention, I provide a flexible wrap for circumscribing a selected portion of the human anatomy and supporting a thermal pack in heat transfer relation to the human anatomy. The improved wrap includes an elongate pliable band of material shaped and dimensioned to circumscribe a selected anatomical portion; container means carried by the elongate band such that said container means is in heat transfer relation with at least a portion of the anatomical portion circumscribed by said band; and, a quantity of thermal material in the container means. The thermal material includes 45.0 to 70.0 weight percent water, and 15.0 to 40.0 weight percent non-water soluble particles each passing through a screen having a size in the range of 30 mesh to 150 mesh.

Figure 1:
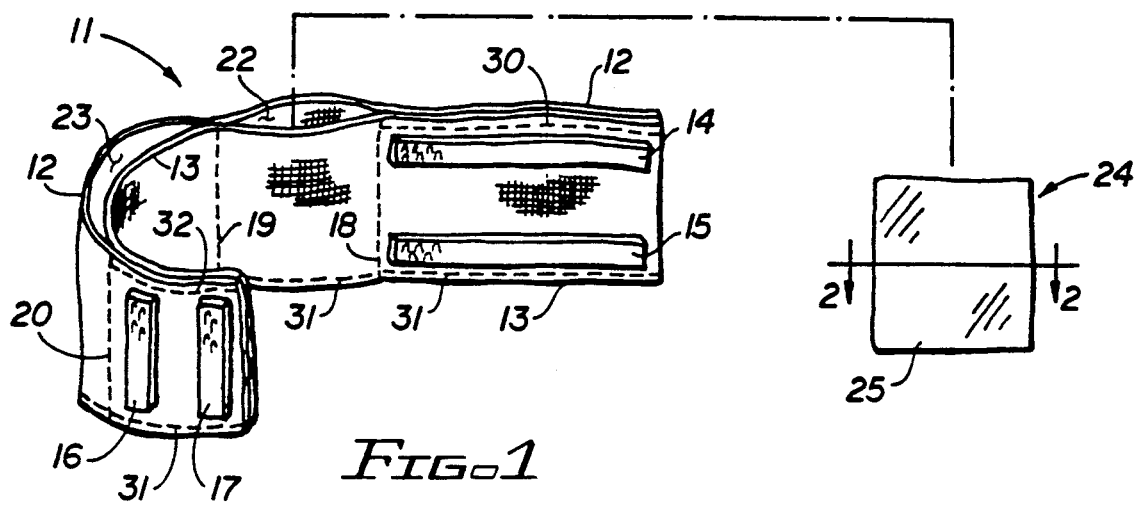
FIG. 1 is a perspective assembly view illustrating a cooling wrap constructed in accordance with the principles of the invention.
Figure 2:
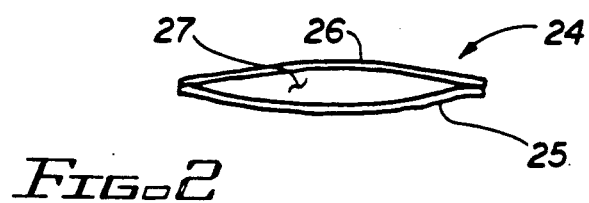
FIG. 2 is a section view taken along section line 2—2 of the thin plastic film sealed liquid container of FIG. 1 and illustrating further construction details thereof; and, FIG. 3 is a top section view illustrating an alternate embodiment of a thin plastic film sealed liquid container which can be utilized in the cooling wrap of FIG. 1.
Figure 3:
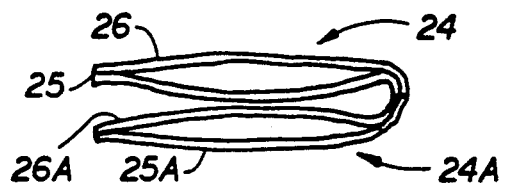

Turning now to the drawings, which depict the presently preferred embodiments of the invention for the purpose of illustrating the practice thereof and not by way of limitation of the scope of the invention, and in which like reference characters refer to corresponding elements throughout the several views, FIG. 1 illustrates a pliable band 11 including a first elongate pliable piece of material 12 connected to a second elongate pliable piece of material 13 along stitching lines 18, 19, 20, 30, 31, 32 such that pockets 22 and 23 are formed. Each pocket 22 and 23 receives a sealed thin plastic film bag containing a freezable liquid composition of the type described below. The thin pliable plastic film bag 24 can be made from polyethylene or any other desired material and includes front panel 25 sealed around its peripheral edge to the peripheral edge of back panel 26. If desired, each pocket 22 and 23 can receive stacks of two or more pliable bags 24. For example, the double layer of bags 24 and 24A shown in FIG. 2 is sized to be received by a pocket 22 or 23. Bag 24A includes front panel 25A sealed around its peripheral edge to the peripheral edge of back panel 26A. Bag 24A, like pliable bag 24, contains the freezable liquid composition of the type described below. The hook and loop VELCRO ® strips 14, 15, 16, 17 are fixedly secured to material 13.

When band 11 is wrapped around the head, leg, forearm or other portion of the human body, strips 14 and 15 are pressed against strips 16 and/or 17 to fixedly removably secure the band 11 on the body. Bands 14 to 17 permit the length of band 11 circumscribing a portion of the human anatomy to be adjusted. In FIG. 1, band 11 is illustrated as having a pair of ends which can be detachably connected by using strips 14 to 17. If desired, band 11 can be a continuous band or loop of material much like the sweat bands which tennis players and other athletes wear.

The freezable liquid composition which I have discovered and which is utilized in bags 24 is an aqueous solution which, on being frozen, forms a pliable solid material that can be manually formed to the contours of a selected portion of the human body. The liquid composition includes water, a gum, an anti-fungal preservative, and a lubricant-like substance which helps prevent frozen water crystals from interlocking to form a solid mass. The composition also includes solid particulate which is not soluble in the liquid portion of the composition. The weight percent of water in the composition is 20.0 to 80.0, preferably 40.0 to 70.0, weight percent. The gum utilized in the liquid composition unexpectedly functions to cause the water to form smaller crystals on freezing and to prevent the crystals from interlocking until a temperature less than the freezing temperature of water is reached. The gums utilized in the invention, whether used alone or in combination with other gums, include gum arabic, xanthan gum, algin derivatives, gum copal, gum elemi, dextrin, maltodextrin, and gelatin. The natural colloidal polysaccharide gum substances exuded by plants or extracted from them by solvents, which are either soluble or swell up with water, and which are salts or complex organic acids yielding hexuronic acids and aldoses on hydolysis are presently preferred, especially xanthan gum and gum arabic. The weight percent of gum in the composition is in the range of 2.0 to 21.0, preferably 5.0 to 10.0 weight percent. 1, 2 Propanediol and like substances are utilized as 3.0 to 11.0 weight percent of the liquid composition and function to act like an oil or lubricant intermediate water crystals and to require that lower temperatures be reached before the water crystals interlock to form a solid mass. A minor effective amount of antifungal or bactericidal chemical is preferably included, but is not required, in the liquid composition to prevent fungi or bacteria from forming in the aqueous solution Numerous such substances are well known in the art Dowicil 200 is presently utilized in the liquid composition utilized in the practice of the invention. Non-water soluble solid particulate is also included in the composition. Each solid particle has a size which permits it to pass through a screen having a size in the range of 30 mesh to 150 mesh, preferably 45 mesh to 100 mesh. The presently preferred particulates, whether utilized singly or in combination with other particulates, are glass beads, styrene beads, and Ottawa sand. The particulate functions to deter the liquid components in the composition from forming into a solid non-pliable mass. It is important that the particles are of a relatively uniform size, within plus or minus 30 mesh of the average size of particle utilized, or are otherwise shaped and dimensioned so that the particles will not tend to interlock to form a stiff or substantially rigid material. Aggregates utilized in the production of concrete typically include different sizes of particulate which tend to interfit or interlock to strengthen the concrete. The invention avoids such an interlocking particle distribution. It is also preferred that the surface of the particles be relatively smooth, both to discourage interlocking of the particles and to help prevent the particles from cutting the thin plastic bag 24 containing the particles and the liquid composition of the invention. In this regard, glass beads and styrene beads are excellent because each are comprised of an essentially spherical piece of material having a smooth surface. On the other hand, the existence of some edges or points on the beads promotes the breakup and pliability of the liquid portion of the composition after the liquid portion has frozen solid.

The following examples are presented by way of example only and not by way of limitation of the scope of the invention.

EXAMPLE 1

The portions of material indicated in TABLE I below were obtained.

TABLE I

| Component | Weight (grams) |
| --- | --- |
| Water (Distilled) | 51.4 |
| Aragum 9000 | 6.87 |
| 1, 2-Propanediol | 7.48 |
| Kelgin | 1.15 |
| Styrene beads (50 mesh) | 32.9 |
| Dowicil 200 | .2 |

The Kelgin and Aragum were mixed dry with the styrene beads. The water was added to this mixture with continual stirring. Nodules of gel formed but dissolved with continued stirring. After the Aragum and Kelgin gums were smoothly mixed and dispersed in the water, the Dowicil was added with stirring. Lastly, the Propanediol was stirred into the mixture. After the Propanediol was stirred into the mixture, the composition was allowed to stand for three hours with occasional stirring every one-half hour. After the final composition stood for three hours with occasional stirring, the composition was placed in a thin pliable plastic polyethylene bag and frozen solid at a temperature of about 23° F. The freezing temperature of the material was about 25° F. The frozen composition appeared to include many small crystals and had a crunchy consistency, much like ice cream sherbet. The frozen composition and the plastic bag containing the composition could be manually contoured around the arm or another selected anatomical portion.

EXAMPLE 2

The portions of material indicated below in TABLE II were obtained.

TABLE II

| Component | Weight (grams) |
| --- | --- |
| Water (Distilled) | 59.5 |
| Aragum 9000 | 8.2 |
| 1, 2 Propanediol | 5.9 |
| Kelgin | 1.76 |
| Styrene Beads | 8.3 |
| Glass Beads | 16.1 |
| Dowicil 200 | .24 |

The Kelgin and Aragum were mixed dry with the styrene beads. Water was added to this mixture with continual stirring. Nodules of gel formed but dissolved 1 with continued stirring. After the Aragum and Kelgin gums were smoothly mixed and dispersed in the water, the Dowicil was added with stirring. Lastly, the Propanediol and glass beads were stirred into the mixture. After the Propanediol and glass beads were stirred into the mixture, the composition was allowed to stand for three hours with occasional stirring every one-half hour. After the final composition stood for three hours with occasional stirring, the composition was placed in a thin pliable plastic polyethylene bag and frozen at a temperature of about 23° F. The freezing temperature of the material was about 23° F. The frozen material composition appeared to include many small crystals and had a crunchy consistency, much like ice cream sherbet. The frozen composition and the plastic bag containing the composition could be manually contoured around the arm or another selected anatomical portion.

The Kelgin HV is sold by KELCO of 20 North Wacker Drive, Chicago, Ill. 60606. The Aragum 9000 is sold by TIC GUMS, INC. of 4609 Richlynn Drive, Belcamp, Md. 21017. The 1, 2-Propanediol is sold by ALDRICH CHEMICAL CO., INC. of 940 West Saint Paul Avenue, Milwaukee, Wis. 53233. The Dowicil 200 is sold by DOW CHEMICAL COMPANY of Midland, Mich. 48640. The styrene beads are sold by BANGS LABORATORIES, INC. of 6 Sue Springs Ct., Carme, Ind. 46032. The glass beads are sold by various companies including JAYGO, WALTER STERN, KING and POTTERS.

EXAMPLE 3

Example 2 is repeated except that 59.5 grams of tap water from Phoenix, Ariz. is substituted for the distilled water. Similar results are obtained.

EXAMPLE 4

Example 2 is repeated except that 24.42 grams of 30 mesh Ottawa sand is substituted for the styrene beads and glass beads. Similar results are obtained.

EXAMPLE 5

Example 2 is repeated except that 5.0 grams of gum copal is substituted for the Aragum 9000 and Kelgin. Similar results are obtained.

EXAMPLE 6

Example 2 is repeated except that 20.0 grams of gum elemi is substituted for Aragum 9000 and Kelgin. Similar results are obtained.

EXAMPLE 7

Example 2 is repeated except that 5.95 grams of glycol is substituted for 1, 2-Propanediol. Similar results are obtained.

EXAMPLE 8

Example 2 is repeated except that 4.00 grams of dextrin is substituted for Aragum 9000. Similar results are obtained.

EXAMPLE 9

Example 2 is repeated except that 14.0 grams of oleoresin is substituted for Aragum 9000. Similar results are obtained.

EXAMPLE 10

Example 2 is repeated except that the styrene beads are sized to pass through screens in the range of forty to seventy mesh and the glass beads are sized to pass through screens in the range of forty to seventy mesh. Similar results are obtained.

Having described my invention in such terms as to enable those skilled in the art to understand and practise it, and having identified the presently preferred embodiments thereof,

I claim:

1. A flexible wrap for circumscribing a selected portion of the human anatomy and supporting a thermal pack in heat transfer relation to the human anatomy, the wrap comprising:
   (a) an elongate pliable band of material shaped and dimensioned to circumscribe a selected anatomical portion;
   (b) container means carried by said elongate band such that said container means is in heat transfer relation with at least a portion of the anatomical portion circumscribed by said band; and,
   (c) a quantity of thermal material in said container means, said thermal material comprising a slurry including
      (i) 40.0 to 70.0 weight percent water,
      (ii) 15.0 to 40.0 weight percent of solid particles each passing through a screen having a size in the range of 30 mesh to 150 mesh,
      (iii) 2.0 to 21.0 weight percent of a gum, and
      (iv) 3.0 to 11.0 weight percent of a water antifreeze composition;
   said slurry on being frozen solid forming a pliable mixture having a crunchy consistency and including said solid particles and frozen crystalline particles.

2. A flexible wrap for circumscribing a selected portion of the human anatomy and supporting a thermal pack in heat transfer relation to the human anatomy, the wrap comprising:
   (a) an elongate pliable band of material shaped and dimensioned to circumscribe a selected anatomical portion;
   (b) container means carried by said elongate bank such that said container means is in heat transfer relation with at least a portion of the anatomical portion circumscribed by said band; and,
   (c) a quantity of thermal material in said container means, said thermal material comprising a slurry including
      (i) 40.0 to 70.0 weight percent water,
      (ii) 15.0 to 40.0 weight percent of non-interlocking solid particles each passing through a screen having a size in the range of 30 mesh to 150 mesh,
      (iii) 2.0 to 21.0 weight percent of a gum, and
      (iv) 3.0 to 11.0 weight percent of a water antifreeze composition,
   said slurry on being frozen solid forming a pliable mixture having a crunchy consistency and including frozen crystalline particles.

3. The wrap of claim 2, wherein said non-interlocking solid particles are a relatively uniform size within plus or minus 30 mesh of the average size of said particles.

4. The wrap of claim 2, wherein said non-interlocking solid particles each consist of at least one material selected from the group consisting of glass, styrene, and sand.

5. A flexible wrap for circumscribing a selected portion of the human anatomy and supporting a thermal pack heat in transfer relation to the human anatomy, the wrap comprising:
   (a) an elongate pliable band of material shaped and dimensioned to circumscribe a selected anatomical portion;
   (b) container means carried by said elongate band such that said container means is in heat transfer relation with at least a portion of the anatomical portion circumscribed by said band; and,
   (c) a quantity of thermal material in said container means, said thermal material comprising a slurry including
      (i) 20.0 to 80.0 weight percent water,
      (ii) 15.0 to 40.0 weight percent of solid particles each passing through a screen having a size in the range of 30 mesh to 150 mesh, and
      (ii) 2.0 to 21.0 weight percent of a gum;
   said slurry on being frozen solid forming a pliable mixture having a crunchy consistency and including said solid particles and frozen crystalline particles.

6. The wrap of claim 5 wherein said particles are non-interlocking.

7. The wrap of claim 6 wherein said particles are of a relatively uniform size within plus or minus 30 mesh of the average size of said particles.

8. The wrap of claim 5 wherein each particle consists of at least one material selected from the group consisting of glass, styrene, and sand.

9. The wrap of claim 6 wherein said particles each have a spherical shape.

10. The wrap of claim 6 wherein said thermal material includes a water antifreeze.

11. The wrap of claim 10 wherein said particles are of a relatively uniform size within plus or minus 30 mesh of the average size of said particles.

12. The wrap of claim 11 wherein said particles each pass through a screen having a size in the range of 45 to 100 mesh instead of passing through a screen having a size in the range of 30 mesh to 150 mesh.

13. The wrap of claim 6 wherein said antifreeze is 1,2- propanediol.

* * * * *